US006592516B2

(12) United States Patent
Lee

(10) Patent No.: US 6,592,516 B2
(45) Date of Patent: Jul. 15, 2003

(54) INTERACTIVE CONTROL SYSTEM OF A SEXUAL DELIGHT APPLIANCE

(76) Inventor: Ching-Chuan Lee, No. 9, Lane 50, Sec. 3, Muhsin Road, Taipei (TW)

( * ) Notice: Subject to any disclaimer, the term of this patent is extended or adjusted under 35 U.S.C. 154(b) by 0 days.

(21) Appl. No.: 09/971,938

(22) Filed: Oct. 9, 2001

(65) Prior Publication Data

US 2003/0069470 A1 Apr. 10, 2003

(51) Int. Cl.[7] .................................................. A61F 5/00
(52) U.S. Cl. ........................................................ 600/38
(58) Field of Search ................................ 128/897, 898; 600/38–41

(56) References Cited

U.S. PATENT DOCUMENTS 6,368,268 B1 * 4/2002 Sandvick et al. ............. 600/38
2002/0065477 A1 * 5/2002 Boyd et al. ................... 601/47

FOREIGN PATENT DOCUMENTS

WO 88/06077 * 8/1988 .................. 600/38

* cited by examiner

*Primary Examiner*—Samuel G. Gilbert
(74) *Attorney, Agent, or Firm*—Troxell Law Offices PLLC

(57) ABSTRACT

An interactive control system of a sexual delight appliance having a signal receiving circuit, a sound analyzing circuit, a status signal input circuit, and a mechanism driving circuit. The signal receiving circuit has an input port for receiving a foreign sound signal. The sound analyzing circuit analyzes and recognizes the received sound signal in terms of the volume, the tone and the speed. The status signal input circuit converts the analyzed sound signal into a plurality of motion signals. The mechanism driving circuit performs the motion signals and allows at least one driving device to produce motions related to the motion signals such that a doll is moved with corresponding motions. In addition, the doll has a built-in sensing feedback device to remotely control another doll at a remote location via a communication net.

9 Claims, 4 Drawing Sheets

INTERACTIVE CONTROL SYSTEM OF A SEXUAL DELIGHT APPLIANCE

BACKGROUND OF THE INVENTION

1. Field of the Invention

The present invention relates to an interactive control system of a sexual delight appliance, and particularly to an interactive control system, which controls the sound and allows a sexual delight appliance to make various motions based on the status of the sound. Furthermore, the interactive control system can remotely control a far end doll to react a motion through a communication net.

2. Description of Related Art

The lovemaking has been covered with a mysterious veil since it was in the very ancient time and, especially, it is a taboo that the oriental is unwilling to talk. Due to the sexual knowledge being prevailed, the lovemaking becomes not mysterious any more so that we can face it with a positive attitude. In fact, according to the psychologist, a proper lovemaking can relieve our pressure and enhance the harmony between a married couple or a loving couple so that the interaction between them may become more intimate and a good livelihood for the couple can be maintained soundly.

The sexual delight appliance, especially the artificial penis or vagina, has brought freshness and amusement to the unchanged sexual life and the couple can enjoy the joy of lovemaking. Besides, an unmarried person or a person without any sexual partner can satisfy the personal sexual desire with the sexual delight appliance. If it is viewed from the positive significance, the sexual delight appliance can eliminate the sex drive of the youngster and decrease the occurrence of sexual crime such that it is possible to avoid the infection of the venereal disease, and especially the AIDS, which is caused by one night love with a stranger in addition to promoting the sexual life for a couple. Thus, the police departments in each country have not looked up the sexual delight appliance as a salacious article gradually. Hence, the sexual delight appliance can be used not only for enhancing the delight between a couple but also for satisfying a sexual need during the strong sexual desire.

Usually, there are two kinds of sexual delight appliances displayed in a sex shop, the static type and the dynamic type. The static type sexual delight appliance provides a appearance imitating a man's penis or a woman's vagina with an unmoved structure. The dynamic type sexual delight appliance provides at least a mechanical device such as an eccentric motor in a doll and the appearance of the doll can be provided with a variety of available shapes for selection. The eccentric motor can be controlled by way of a controller adjusting the speed thereof or the twisting direction thereof so as to reach the purpose of stimulating the sensitive zone. Because the conventional sexual delight appliance mostly is designed for a single person or for being controlled by another person, it is not possible to offer mutual actions between a married couple or a loving couple. For instance, if a married couple or a loving couple are living at two different places respectively over a long period of time, both of them are unable to have a normal sexual life as soon as they have sex desire because of their far away from each other. As a result, it occurs the illegal love affair frequently or consoling oneself individually, and it is involved in an important reason that the interaction between the couple is inferior.

SUMMARY OF THE INVENTION

An object of the present invention is to provide an interactive control system of a sexual delight appliance, which comprises a signal receiving circuit, a sound analyzing circuit, a status signal input circuit and a mechanism driving circuit, such that the sexual delight appliance can be controlled to perform various motions corresponding to the sound emitted by the user.

Another object of the present invention is to provide an interactive control system of a sexual delight appliance, which further comprises a built-in sensing feedback device in the sexual delight appliance to remotely control a far end sexual delight appliance via a communication net.

BRIEF DESCRIPTION OF THE DRAWINGS

The present invention can be more fully understood by referencing to the following detailed description and accompanying drawings, in which.

DETAILED DESCRIPTION OF THE PREFERRED EMBODIMENTS

Figure 1:
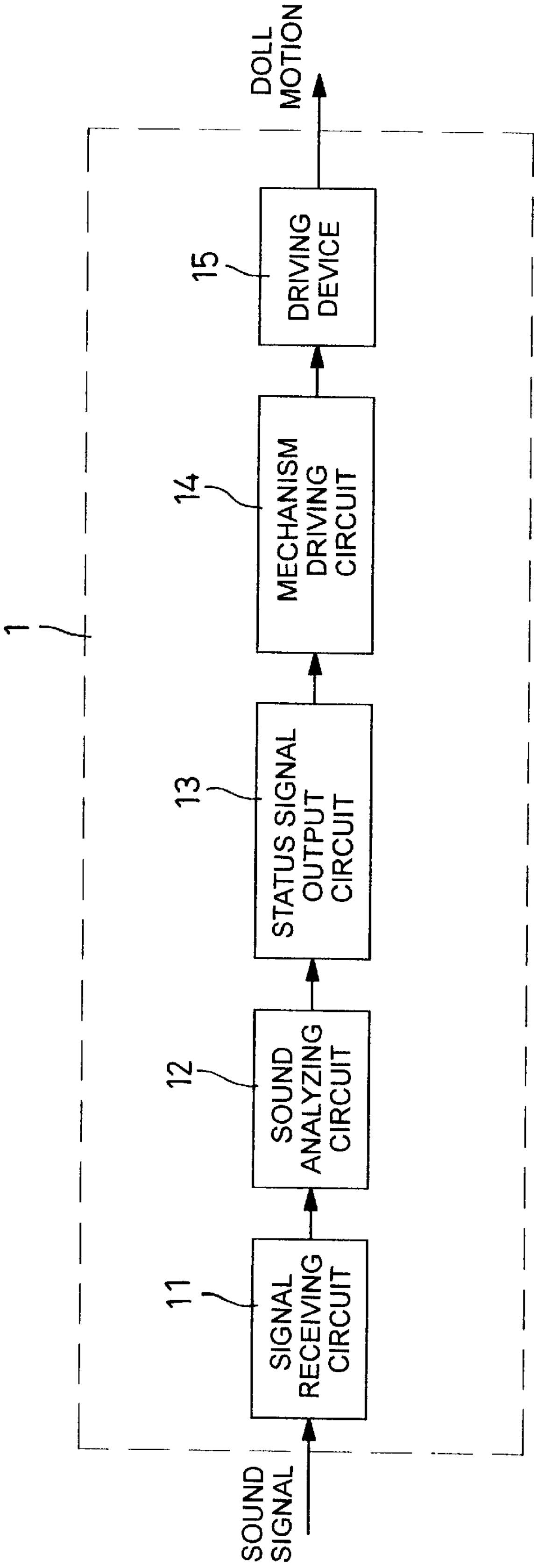
FIG. 1 is a system block diagram of a basic structure of an interactive control system in a sexual delight appliance according to the present invention.

Referring to FIG. 1, a basic structure of an interactive control system of a sexual delight appliance according to the present invention is illustrated and the sexual delight appliance can be provided with a shape as desired based on the actual need. Of course, the sexual delight appliance can be an artificial penis or vagina and it will be designated as a doll hereinafter. Wherein, a signal receiving circuit 11 is provided in the doll to receive a foreign sound signal via an input port and then a sound analyzing circuit 12 is arranged to recognize and analyze the sound signal such that a result can be obtained through the analysis in terms of the volume, the tone, and the speed thereof. A state signal output circuit 13 sends out different motion signals corresponding to the result to allow a mechanism driving circuit 14 performing preceding motion signals such that at least a driving device 5 such as an eccentric motor, a gear mechanism, and etc. can generate a motion such as moving forward, moving backward, compressing, loosening, turning, vibrating, or sprinkling. Accordingly, the doll 1 can react a corresponding motion with an effect of unexpected motion variation. In fact, the input port of the signal receiving circuit 11 may receive any sound signal from a product with a sound output such as a television, a stereo, or a radio, or the sound sent out by the user himself/herself or another person directly. Hence, the doll 1 can produce a motion by way of the steps of sound receiving and analyzing, . . . , and etc. and this means the doll 1 and the user have a single way of interactive relation.

Figure 2:
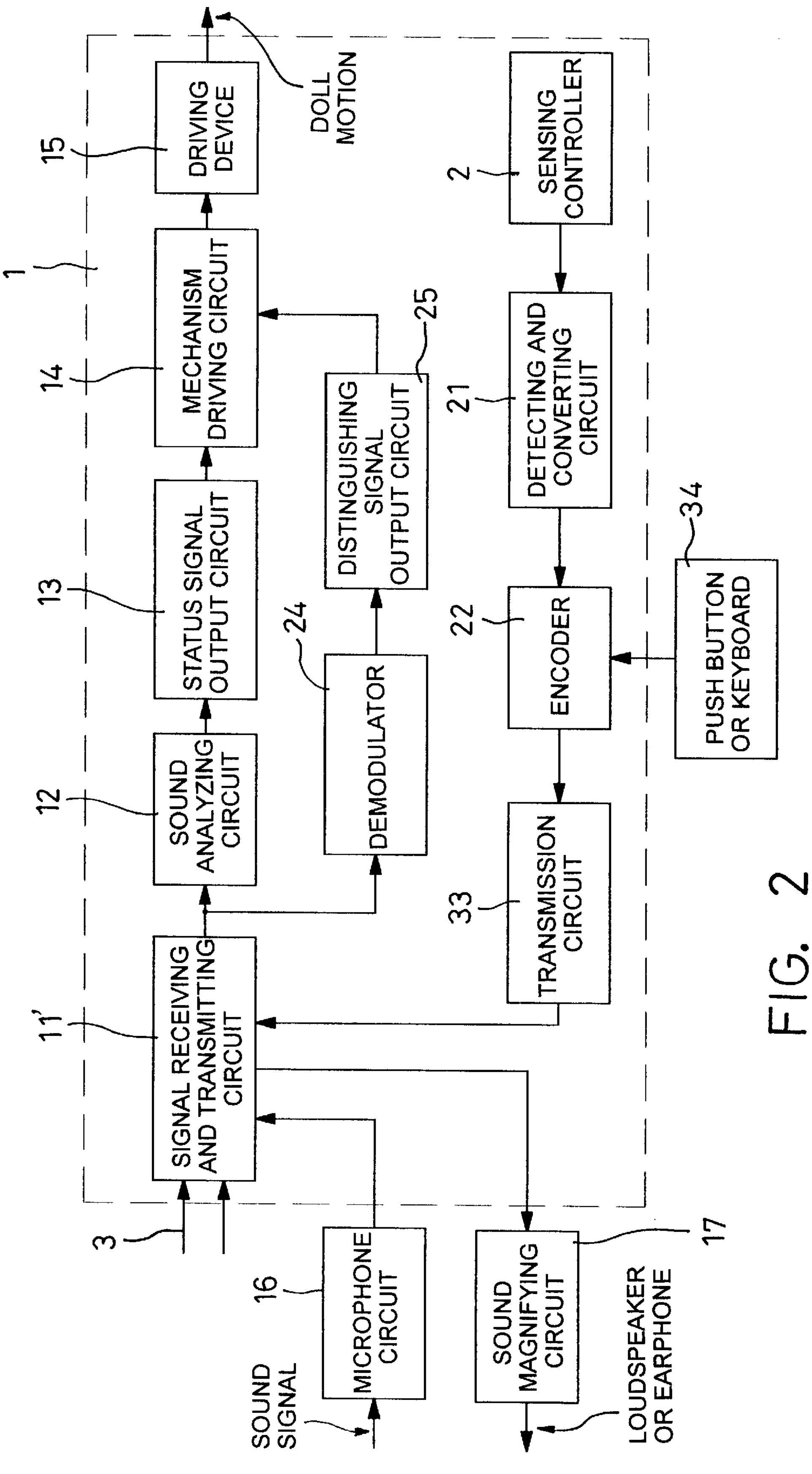
FIG. 2 is a system block diagram in a preferred embodiment of the present invention.

Referring to FIG. 2, Besides, in order to enhance the function of sensing and feeding back, a sensing feedback device can be mounted in the doll 1 and the sensing and feeding back device at least comprises a sensing controller 2 such as a pressure switch, a variable resistance type switch, and etc. such that the signal is converted into corresponding control signal such as DTMF code or the control code of any other communication protocol by way of a selected sensing controller 2 being pressed or touched with detecting and a converting circuit 21 detecting a status of operation such as the magnitude of pressure, the number of times of pressing or the position of pressing. The controlled signal is encoded with an encoder 22 and then the encoded controlled signal is transmitted to a signal receiving and transmitting circuit 11', which is included in the preceding signal receiving circuit 11, through a transmission circuit 23. Further, the encoded controlled signal is then transmitted to the doll 1, which is at a far end and connects with the communication net 3, and is decoded by a demodulator 24 after the signal receiving and transmitting circuit 11' receiving the encoded controlled signal. The decoded controlled signal then passes through an output signal distinguishing circuit 25 and an expected motion can be confirmed as soon as the decoded controlled signal is treated with the distinguishing circuit 25 such that the output signal distinguishing circuit 25 can order the preceding mechanism driving circuit 14 to execute an instruction of moving the driving device. Therefore, due to the function of the sensing feedback device, a couple of users can play the doll 1 mutually in spite of both users being far from each other and they can feel an expected motion of the other side immediately via the communication net sending the controlled signal such that the couple of users can perform an interaction intimately.

As the foregoing, the interactive control system of the present invention can perform an interactive remote control mutually by way of the communication net 3. Referring to FIGS. 2 to 5, the signal receiving and transmitting circuit 11' provides an input port to connect with the communication net 3 such as a local phone net 31, a mobile phone net 32, or the internet 33.

As it is shown in FIGS. 3A and 4 again, the local phone net 31 connects with a traditional telephone set 311 and the input port of the doll 1 connects with the local phone net 31 in parallel such that the sound signal can be transmitted to the doll 1 of the other side at the far end so as to remotely control the expected motion of the doll 1 of the other side and achieve an interactive function of mutual comfort for each other.

As it is shown in FIGS. 3B and 4 again, the local phone net 31 connects with the input port of the doll 1 directly and the signal receiving and transmitting circuit 11' connects with a microphone circuit 16 and a sound magnifying circuit 17 externally such that the sound signal can be sent out by way of the microphone circuit 16, the signal receiving and transmitting circuit 11', and the local phone net 31 and the doll 1 at the far end can react a motion after receiving the sound signal so as to perform a function of interaction too.

Figure 3A:
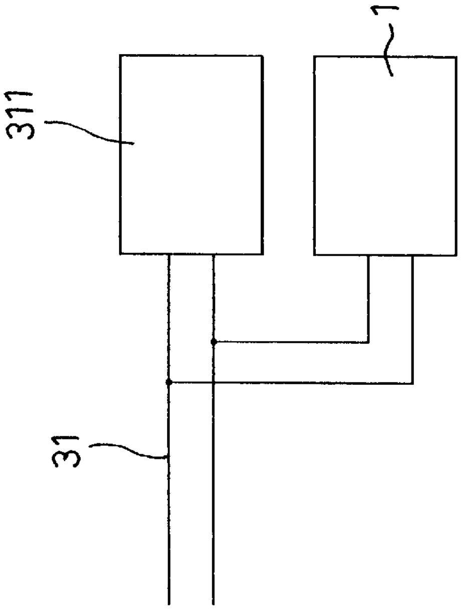
FIGS. 3A to 3C are diagrammatic view illustrating the interactive control system of the present invention connecting with a communication product respectively.
Figure 3B:
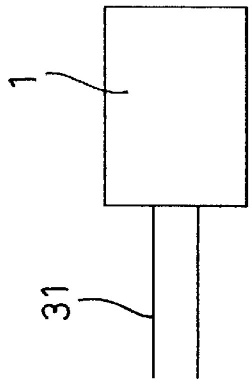
Figure 3C:
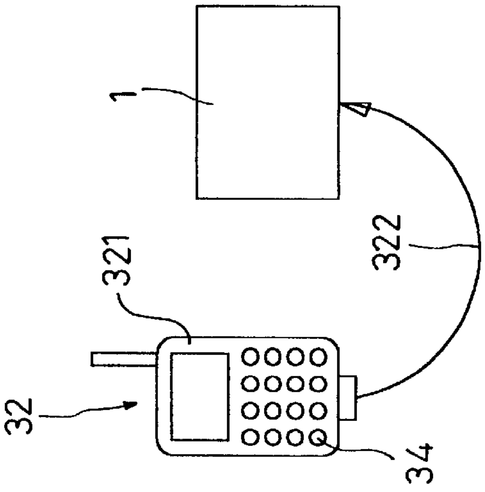
Figure 4:
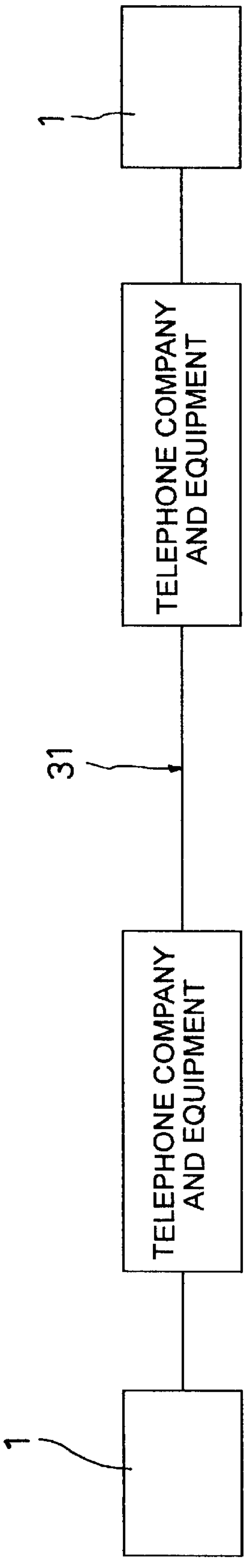
FIG. 4 is a diagrammatic view illustrating the interactive control system of the present invention being applied to the local telephone net.
Figure 5:
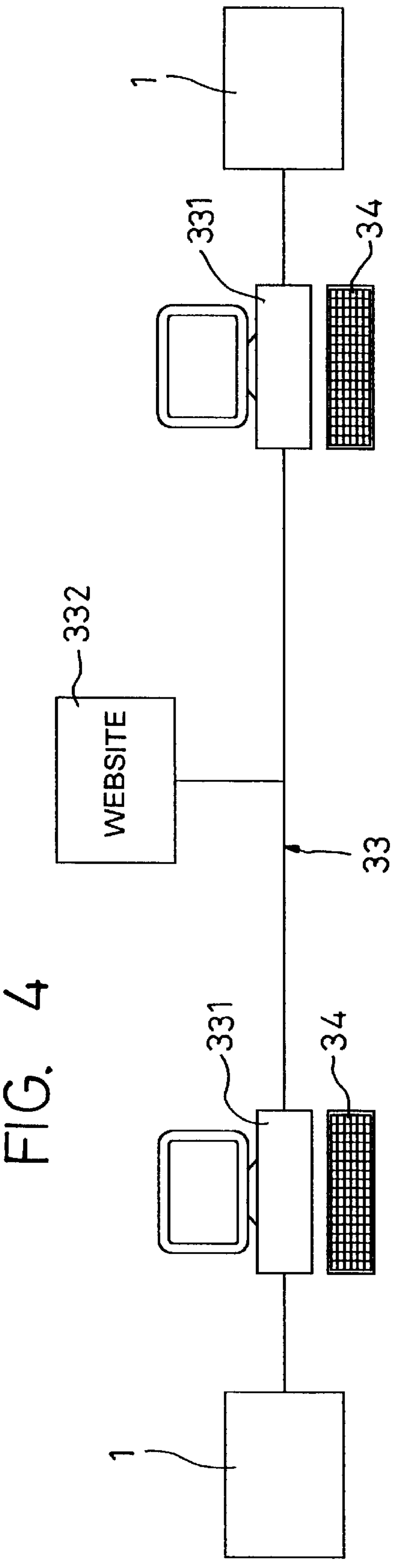
FIG. 5 is a diagrammatic view illustrating the interactive control system of the present invention being applied to the internet.

Similarly, a connecting port of the mobile phone 321 connects with the input port of the doll 1 via a signal wire 322 as shown in FIG. 3C to transmit the sound signal to the input port of another doll 1 at the far end such that the doll 1 of the other side can generate a corresponding reactive motion to achieve the remote control and the function of interaction.

Moreover, the interactive control system of the present invention is possible to be applied in the internet 33. In practice, the input port of the doll 1 connects with input/output ports available in a computer 331 such as a RS-232 interface, a USB interface, a sound effect card interface, a print interface, . . . , and etc. so that the sound signal can be transmitted to the doll 1 of the other side to produce an expected motion and achieve a far end remote control mutually by way of a software processing control or the sound effect card via on line conversation forthwith.

Furthermore, referring to FIG. 2 again, the foregoing traditional telephone set 311, the mobile phone 321 and the computer 331 are provided with press buttons or a keyboard 34 and the user can press different buttons or the keyboard 34 to produce a controlled signal being encoded with the encoder 22 and the encoded controlled signal passes through the signal receiving and transmitting circuit 11' and the communication net 3 via a transmission circuit 23 such that the doll 1 of the other side can generate an expected motion and it is possible to control the motion of the doll 1 of the other side by way of the sound and the controlled signal at the same time. Thus, a far end remote control can be performed through the sensing controller 2, press buttons, or the keyboard 34 during both sides being occupied with endless whispers of love. Hence, the interactive control system of the present invention to give the doll 1 an artificial intelligence and this is a great breakthrough provided by the present inventor.

Although the preceding mode with regard to the far end remote control or the sensing feedback device is based on a married couple or a loving couple who stay at two different places distant from each other, actually the present invention can be applied to two persons having never seen each other. For instance, a person can enter the internet 33 through a computer 331 to browse a website 332 which has a voice chat room or a related entertainment website 332 and the doll 1 of the other side can receive a voice or a control signal to react a corresponding movement. Under this circumstance, both sides having never seen can offer sexual need to each other, and, meanwhile, it can actualize the pseudo-sex occurring in the past to reduce the moral problem resulting from the one night love, the infection of venereal disease and even the chance of committing a crime.

Accordingly, it is appreciated that the interactive control system of a sexual delight appliance according to the present invention can be used by a personal individual to self-control the sensing feedback device or perform by way of a sound signal sent from outside or the self-sound uttered by the user such that the doll can react a movement to obtain a personal relief for the user. In addition, the present invention can be applied to a married couple or a loving couple often separately staying at two different places and both sides own a doll respectively to connect with each other through a communication net such that the doll at the opposite side can generate a movement desired by the self side to relieve the sex needs of both sides with a real feeling respectively by way of transmitting sound signals or controlling the sensing controller, push buttons, or the keyboard. Moreover, the both sides can enhance the interactions and the mutual intimacy as soon as the sound communication between both sides is added during the dolls being operated. Furthermore, the user can talk with a web-mate through a voice chat room of a website in a website or through a related entertainment website so as to control the doll via the voices of or control signals being sent by the websites and the doll can react corresponding movements so as to relieve the sexual desire of the user such that the sexual crime and the venereal disease can be effectively prevented from spreading over. Therefore, the interactive control system of a sexual delight appliance according to the present invention virtually provides a humanized interactive function, which is not possible for the prior art to reach completely.

While the invention has been described with reference to a preferred embodiment thereof, it is to be understood that modifications or variations may be easily made without departing from the spirit of this invention, which is defined by the appended claims.

What is claimed is:

1. An interactive control system for a sexual delight appliance for use with at least one doll, comprising at least one interactive control module having:

a) a signal receiving circuit having an input port for receiving a sound signal from outside;

b) a sound analyzing circuit, analyzing and recognizing the received sound signal based on a volume a tone and a speed thereof respectively;

c) a status signal input circuit, converting the analyzed sound signal into a plurality of motion signals;

d) a mechanism driving circuit, evaluating the motion signals and controlling at least one mechanism driving device to move the at least one doll relative to the motion signals;

e) a sensing feedback device having;

i) at least one sensor controller, being pressed or touched to generate a signal;

ii) a detecting and converting circuit, detecting the signal and converting the signal into a corresponding control signal;

iii) an encoder, encoding the control signal;

iv) transmission circuit, sending the encoded control signal to the signal receiving circuit;

v) a decoder, decoding the control signal coming from the signal receiving circuit; and vi) an output signal distinguishing circuit, distinguishing the decoded control signal and converting the decoded control sign into various motion signals;

whereby, the mechanism driving circuit evaluates the motion signals and controls the at least one driving device to move the at least one doll relative to the motion signals.

2. The interactive control system for a sexual delight appliance for use with at least one doll according to claim 1, wherein the input port is connected with a communication net and the encoded control signals are sent out and received by the communication net, the received control signals are converted by the decoder and the output signal distinguishing circuit to produce a desired motion, such that a plurality of interactive control modules, each being connected to at least one doll, communicate through the communication net.

3. The interactive control system for sexual delight appliance for use with at least one doll according to claim 2, wherein the communication net is local telephone net, a mobile phone net, or an internet.

4. The interactive control system for a sexual delight appliance for use with at least one doll according to claim 3, wherein the input port is connected with the local phone net.

5. The interactive control system for a sexual delight appliance for use with at least one doll according to claim 3, wherein the input port provides a signal line to connect with a connecting port of a mobile phone, such that a control signal is sent through the mobile phone net.

6. The interactive control system for a sexual delight appliance for use with at least one doll according to claim 3, wherein the input port connects with an input/output port of a computer and the encoded control signal remotely controls the motion of the at least one doll.

7. The interactive control system for a sexual delight appliance for use with at least one doll according to claim 6, wherein the at least one doll is moved by way of a control signal sent out by a website.

8. The interactive control system for a sexual delight appliance for use with at least one doll according to claim 1, wherein the encoder receives the control signal generated by pressing a button on one electronic device selected from the group consisting of a telephone, a mobile phone, and a computer.

9. The interactive control system for a sexual delight appliance for use with at least one doll according to claim 1, wherein the control signal is DTMF code.

* * * * *